United States Patent
Liang

(10) Patent No.: US 8,288,692 B2
(45) Date of Patent: Oct. 16, 2012

(54) PORTABLE WARMER

(76) Inventor: ShengQuan Liang, Foshan (CN)

( * ) Notice: Subject to any disclaimer, the term of this patent is extended or adjusted under 35 U.S.C. 154(b) by 1353 days.

(21) Appl. No.: 11/998,707

(22) Filed: Nov. 29, 2007

(65) Prior Publication Data

US 2008/0296286 A1   Dec. 4, 2008

Related U.S. Application Data

(63) Continuation-in-part of application No. 11/895,439, filed on Aug. 23, 2007.

(30) Foreign Application Priority Data

Jun. 4, 2007   (CN) .......................... 2007 1 0074814

(51) Int. Cl.
*H05B 3/34*   (2006.01)
*F24F 7/00*   (2006.01)

(52) U.S. Cl. ........................................ 219/528; 392/339

(58) Field of Classification Search .......... 219/385–387, 219/528, 529, 530, 538–549; 392/339–341; 126/263.06, 263.07

See application file for complete search history.

(56) References Cited

U.S. PATENT DOCUMENTS

| | | | | | |
|---|---|---|---|---|---|
| 2,223,154 | A | * | 11/1940 | Thornton-Norris | 392/443 |
| 3,014,117 | A | * | 12/1961 | Madding | 392/443 |
| 4,868,898 | A | * | 9/1989 | Seto | 219/528 |
| 5,932,129 | A | * | 8/1999 | Hyatt | 219/528 |
| 6,031,212 | A | * | 2/2000 | Westerman et al. | 219/535 |

* cited by examiner

*Primary Examiner* — Sang Paik
(74) *Attorney, Agent, or Firm* — Raymond Y. Chan; David and Raymond Patent Firm

(57) ABSTRACT

A warmer bag includes a casing, a warmer bag, a heating arrangement including a heating element for heating up a fluid contained in the warmer bag at an usable temperature, and a safety arrangement electrically coupling with the heating arrangement, wherein when the heat exchanging fluid is heated above the usable temperature, the safety arrangement automatically cuts off an electrical connection between the heating element and the external power source for preventing the fluid from being overheated.

3 Claims, 8 Drawing Sheets

PORTABLE WARMER

CROSS REFERENCE OF RELATED APPLICATION

This is a Continuation-In-Part application of a non-provisional application having an application Ser. No. 11/895,439 and a filing date of Aug. 23, 2007.

BACKGROUND OF THE PRESENT INVENTION

1. Field of Invention

The present invention relates to a warmer, and more particularly to a portable warmer, wherein a warmer bag is received in a casing to safely warm up the heat exchanging fluid in the warmer bag through a safety arrangement such that when the heat exchanging fluid is heated above an usable temperature, the safety arrangement automatically cuts off an electrical connection between the heating element and the external power source for preventing the heat exchanging fluid from being overheated.

2. Description of Related Arts

During winter time, most people would like to use some warmer apparatus, such as electric heaters, in order to keep themselves warm. However, such warmer apparatus requires an electric power and has a relatively bulky size that the user cannot carry the warmer apparatus everywhere.

One kind of small and portable heating device, called warm water bag comprises a sealing bag, which is made of waterproof material such as plastic, having an inner cavity and an opening. In order to use the water bag, the user has to fill up the hot water into the inner cavity of the bag. Therefore, the user is able to hold the water bag close to the body of the user. In other words, the water inside the cavity gradually dispenses its heat through the sealing bag, so that the user can put the water bag to part of body, such as hands or feet, to keep himself or herself warm.

An improved water bag is made that the water bag is adapted to be placed in a microwave oven to heat up the water inside the water bag. Likewise, a built-in heating element is mounted into the water bag to heat up the water inside the water bag.

However, the traditional water bag is inconvenient for people to use. Since the hot water is gradually cooling down in a timely manner, the water bag cannot provide the warming ability after a short period of time. Then, the user must pour out the water inside the sealing bag and refill the hot water. In other words, the user must repeatedly refill the hot water frequently, which is very inefficient and inconvenient.

In the other hand, it is convenient for the user to heat up the water inside the sealing bag by microwave oven. However, it is relatively dangerous for the user when the water inside the sealing bag is overheated. Accordingly, few seconds of contacting with the hot water will cause a serious burn. The overheated water inside the sealing bag will also cause a serious explosion.

Likewise, by electrically connecting the heating element with the external power source, the water inside the sealing bag can be gently heated up by the heating element. However, when the water is heated, the volume of the water is expanded. When the water expands at a predetermined volume larger than the capacity of the sealing bag, the sealing bag will be forced to be popped and the hot water will be leaked from the sealing bag. Since the heating element is electrically connected to the power source, the hot water leaking from the sealing bag may cause an electrical short circuit or even a serious electric shock to the user. In other words, the user needs to find more secure and safe way to keep warm by using the water bag.

SUMMARY OF THE PRESENT INVENTION

A main object of the present invention is to provide a portable warmer, wherein the heating operation for the warmer bag is monitored by the safety arrangement to prevent the fluid inside the bag from being overheated.

Another object of the present invention is to provide a portable warmer, wherein the warmer bag is small and portable for people to use.

Another object of the present invention is to provide a portable warmer, wherein the warmer bag provides two different security apparatus to guarantee its using safety.

Another object of the present invention is to provide a portable warmer, which does not require to alter the original structural design of the warmer bag, so as to minimize the manufacturing cost of the warmer bag incorporating with the casing.

Another object of the present invention is to provide a portable warmer, wherein no expensive or complicated structure is required to employ in the present invention in order to achieve the above mentioned objects. Therefore, the present invention successfully provides an economic and efficient solution for providing a safety configuration for the portable warmer to prevent the fluid inside the warmer bag from being overheated.

Accordingly, in order to accomplish the above object, the present invention provides a warmer bag comprises:

a casing having a receiving compartment;

a warmer bag comprising a bag body defining a fluid cavity therein, and a heat exchanging fluid sealed and contained in the fluid cavity of the bag body;

a heating arrangement comprising a power cable having a power outlet extended out of the casing for electrically connecting with an external power source and a power adapter extended into the receiving compartment, an electric terminal provided at the bag body, and a heating element which is supported in the fluid cavity and is electrically coupled with the electric terminal, wherein when the warmer bag is disposed in the receiving compartment, the power adapter of the power cable is detachably and electrically coupled with the electric terminal for electrically connecting the heating element with the external power source so as to heat up the heat exchanging fluid at a predetermined usable temperature; and a safety arrangement electrically coupling with the heating arrangement, wherein when the heat exchanging fluid is heated above the usable temperature, the safety arrangement automatically cuts off an electrical connection between the heating element and the external power source for preventing the heat exchanging fluid from being overheated.

Accordingly, the safety arrangement comprises a contact switch provided at the casing such that when the warmer bag is disposed in the casing during the heating operation, the contact switch is automatically actuated to cut off the electrical connection between the heating element and the external power source in responsive to the expansion of the heat exchanging fluid.

These and other objectives, features, and advantages of the present invention will become apparent from the following detailed description, the accompanying drawings, and the appended claims.

DETAILED DESCRIPTION OF THE PREFERRED EMBODIMENT

Figure 1:
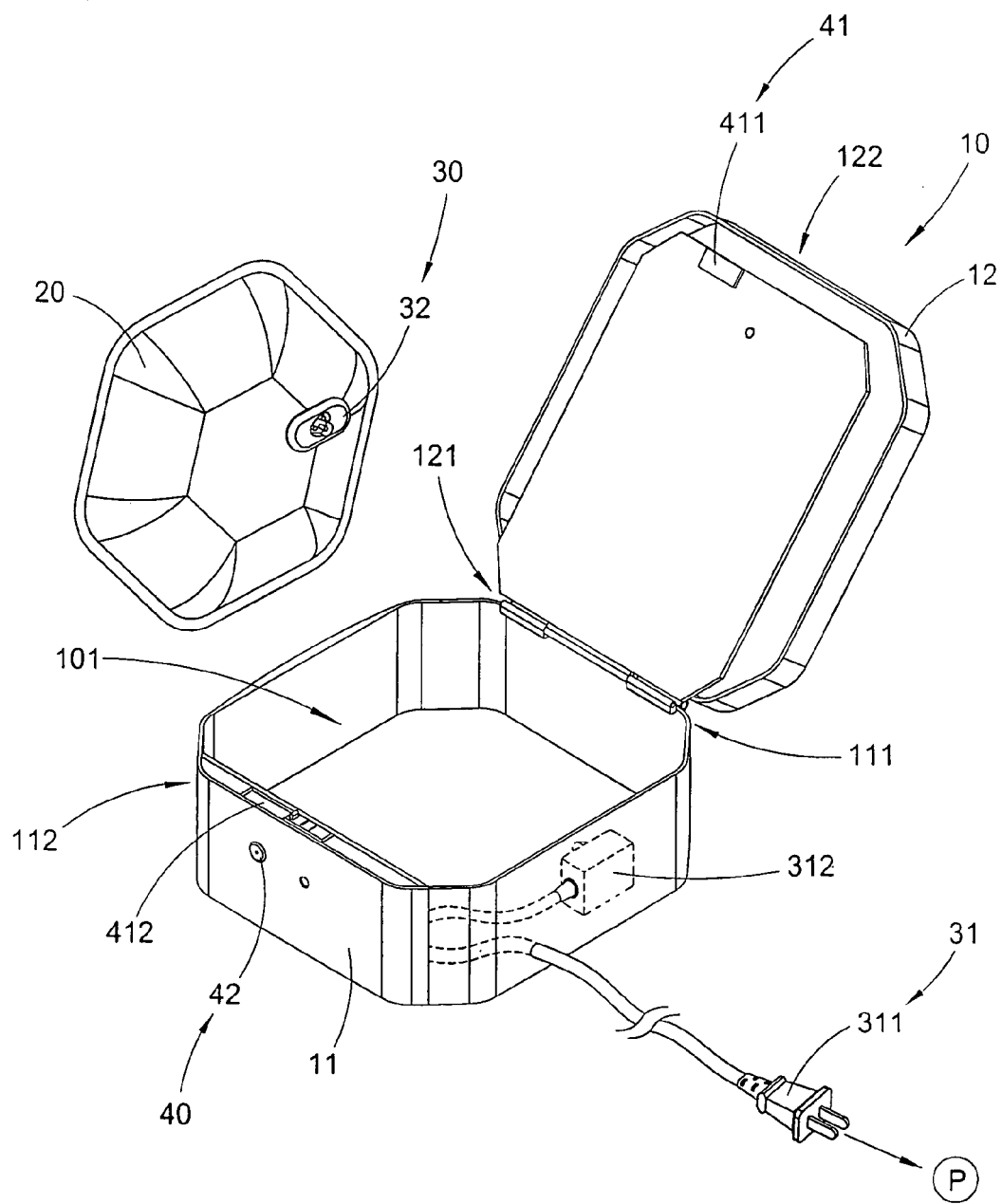
FIG. 1 is a perspective view of a portable warmer according to a preferred embodiment of the present invention.
Figure 4:
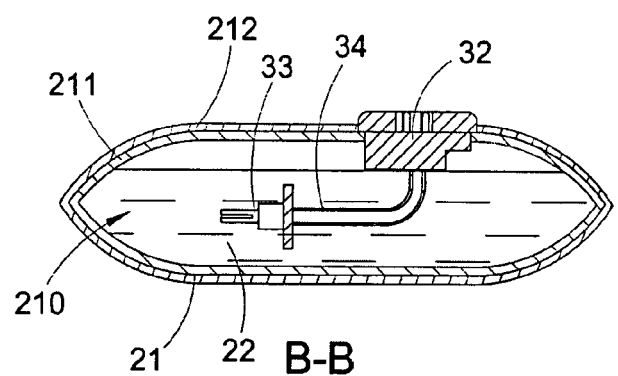
FIG. 4 is a sectional view of the warmer bag according to the above preferred embodiment of the present invention, illustrating the position of the heating element.

Referring to FIGS. 1 and 4 of the drawings, a portable warmer according to a preferred embodiment of the present invention is illustrated, wherein the portable warmer comprises a casing 10 having a receiving compartment 101, and a warmer bag 20 comprising a bag body 21 defining a fluid cavity 210 therein and a heat exchanging fluid 22 sealed and contained in the fluid cavity 210 of the bag body 20. According to the preferred embodiment, the heat exchanging fluid 22 is saline water containing approximately 1% salt dissolving in water by weight.

The portable warmer further comprises a heating arrangement 30 and a safety arrangement 40.

The heating arrangement 30 comprises a power cable 31, an electric terminal 32 provided at the bag body 21, and a heating element 33. The power cable 31 has a power outlet 311 extended out of the casing 10 for electrically connecting with an external power source P and a power adapter 312 extended into the receiving compartment 101.

The heating element 33 is supported in the fluid cavity 210 and is electrically coupled with the electric terminal 32, wherein when the warmer bag 20 is disposed in the receiving compartment 101, the power adapter 312 of the power cable 31 is detachably and electrically coupled with the electric terminal 32 for electrically connecting the heating element 33 with the external power source P so as to heat up the heat exchanging fluid 22 at a predetermined usable temperature.

The safety arrangement 40 is electrically coupling with the heating arrangement 40, wherein when the heat exchanging fluid 22 is heated above the usable temperature, the safety arrangement 40 automatically cuts off an electrical connection between the heating element 33 and the external power source P for preventing the heat exchanging fluid 22 from being overheated.

According to the preferred embodiment, the bag body 21 of the warmer bag 20 is made of flexible material that the warmer bag 20 seals and contains the heat exchanging fluid 22 in a stretchable manner. The bag body 21 is constructed by a plurality of layers as shown in FIG. 4, wherein the innermost layer 211 is made of waterproof material to seal the heat exchanging fluid 22 within the fluid cavity 210 while the outermost layer 212 is made of soft material to be touched by the user body.

Accordingly, when the heat exchanging fluid 22 is at the usable temperature, the heat exchanging fluid 22 expands its volume in comparison with the heat exchanging fluid 22 at a normal room temperature. According to the preferred embodiment, the heat exchanging fluid 22 is heated up at approximately 70° C. In addition the bag body 21 will be expanded approximately 1 to 2 cm by size when the heat exchanging fluid 22 is heated up from the normal room temperature to 70° C.

As shown in FIG. 4, the heat exchanging fluid 22 is partially filled in the bag body 21 of the warmer bag 20 that when the warmer bag 20 is disposed in the casing 10, a bottom portion of the warmer bag 20 is filled with the heat exchanging fluid 22 while an upper portion of the warmer bag 20 is filled with gas. In other words, when the warmer bag 20 is lain flat in receiving compartment 101 of the casing 10, the heating element 33 is submerged at the heat exchanging fluid 22. Therefore, when the heat exchanging fluid 22 is heated up, the bag body 21 provides enough room for the volume-expansion of the heat exchanging fluid 22 without popping the bag body 21.

The heating arrangement 30 further comprises a retention arm 34 extended from the electric terminal 32 to the heating element 33 to retain the heating element 33 at a position that the heating element 33 is submerged at the heat exchanging fluid 22 to effectively heat up the heat exchanging fluid 22.

Figure 2:
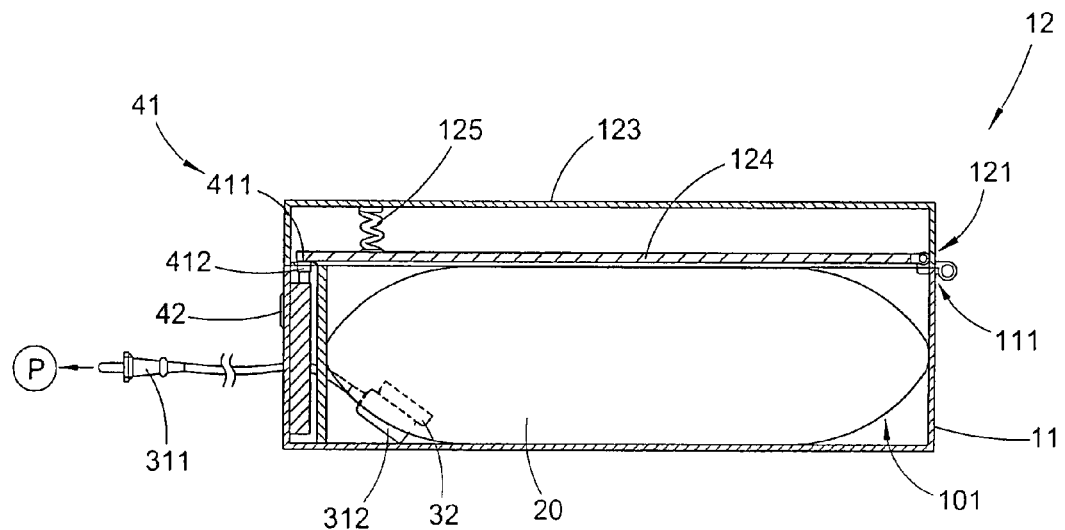
FIG. 2 is a schematic view of the warmer bag disposed in the casing during heating operation according to the above preferred embodiment of the present invention.

As shown in FIG. 2, the safety arrangement 40 comprises a contact switch 41 provided at the casing 10 to cut off the electrical connection between the heating element 33 and the external power source P when the heat exchanging fluid 22 is heated at the usable temperature. The contact switch 41 is electrically coupled with the power cable 31 between the power outlet 311 and the power adapter 312 such that the contact switch 41 cuts off the electrical connection between the power outlet 311 and the power adapter 312.

According to the preferred embodiment, the casing 10 comprises a base housing 11 and a cover housing 12 pivotally coupling with the base housing 11 to enclose the receiving compartment 101. The base housing 11 has a first housing edge 111 and an opposed second housing edge 112. The cover housing 12 has a pivot edge 121 pivotally coupling with the first housing edge 111 of the base housing 11 and a folding edge 122 folded to align with the second housing edge 112 of the base housing 11.

Accordingly, the contact switch 41 comprises a first contacting terminal 411 provided at the second housing edge 112 of the base housing 11 and a second contacting terminal 412 provided at the folding edge 122 of the cover housing 12 to align with the first contacting terminal 411. Therefore, when the cover housing 12 is pivotally folded on the base housing 11, the second contacting terminal 412 contacts with the first contacting terminal 411 so as to close the electrical connection between the power outlet 311 and the power adapter 312.

Figure 3:
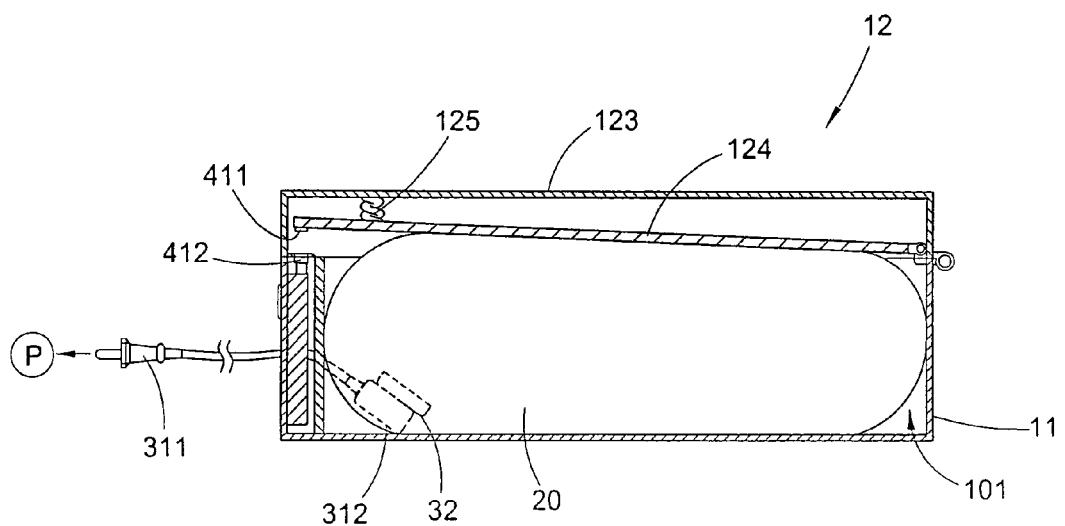
FIG. 3 is a schematic view of the warmer bag disposed in the casing during cut off operation according to the above preferred embodiment of the present invention.

When the heat exchanging fluid 22 is at the normal room temperature, the cover housing 12 is pivotally folded to contact the second contacting terminal 412 with the first contacting terminal 411 to close the electrical connection between the heating element 33 and the external power source P, as shown in FIG. 2. When the heat exchanging fluid 22 is at the usable temperature, the warmer bag 20 is expanded to move the second contacting terminal 412 away from the first contacting terminal 411 so as to cut off the electrical connection between the heating element 33 and the external power source P, as shown in FIG. 3. In other words, when the heat exchanging fluid 22 is at the normal room temperature, the cover housing 12 can be fully covered on top of the base housing 11 to conceal the receiving compartment 101. Once the heat exchanging fluid 22 is heated up at the usable temperature, the warmer bag 20 is expanded with a predetermined volume enough to push the second contacting terminal 412 away from the first contacting terminal 411. It is worth to mention that when the warmer bag 20 is disposed in the casing 10, the two sides of the warmer bag 20 are biased against two inner sidewalls of the casing 10 respectively. Therefore, the warmer bag 20 will be expanded at its transverse direction.

As shown in FIGS. 2 and 3, the cover housing 12 comprises an outer shelter 123 pivotally folded on the base housing 11 to enclose the receiving compartment 101, and an inner pivot cover 124 pivotally coupling with the outer shelter 123, wherein the second contacting terminal 412 is provided at the inner pivot cover 124 such that when the warmer bag 20 is expanded to pivotally and upwardly move the inner pivot cover 124 for moving the second contacting terminal 412 away from the first contacting terminal 411, the outer shelter 123 is remained at its position to enclose the warmer bag 20 in the receiving compartment 101. The inner pivot cover 124 is pivotally coupled with the outer shelter 123 at the pivot edge 121 thereof.

The cover housing 12 further comprises a resilient element 125 supported between the outer shelter 123 and the inner pivot cover 124 for applying an urging force against the inner pivot cover 124 to ensure the second contacting terminal 412 being contacted with the first contacting terminal 411 when the heat exchanging fluid 22 is heated under the unable temperature.

According to the preferred embodiment, the safety arrangement 40 further comprises a signal generator 42 provided at an outer side of the base housing 11 and electrically coupled with the contact switch 41 for generating a notifying signal when the second contacting terminal 412 is moved apart from the first contacting terminal 411. The signal generator 42 comprises a LED light for generating a light signal as the notifying signal and/or a buzzer for generating a sound signal as the notifying signal. Therefore, the signal generator 42 will notify the user the warmer bag 20 is ready to use when the heat exchanging fluid 22 is heated up at the usable temperature. In addition, since the contact switch 41 prevents the heat exchanging fluid 22 from being overheated, the user is able to remove the warmer bag 20 without being burned by the warmer bag 20 once the notifying signal is generated.

Figure 5:
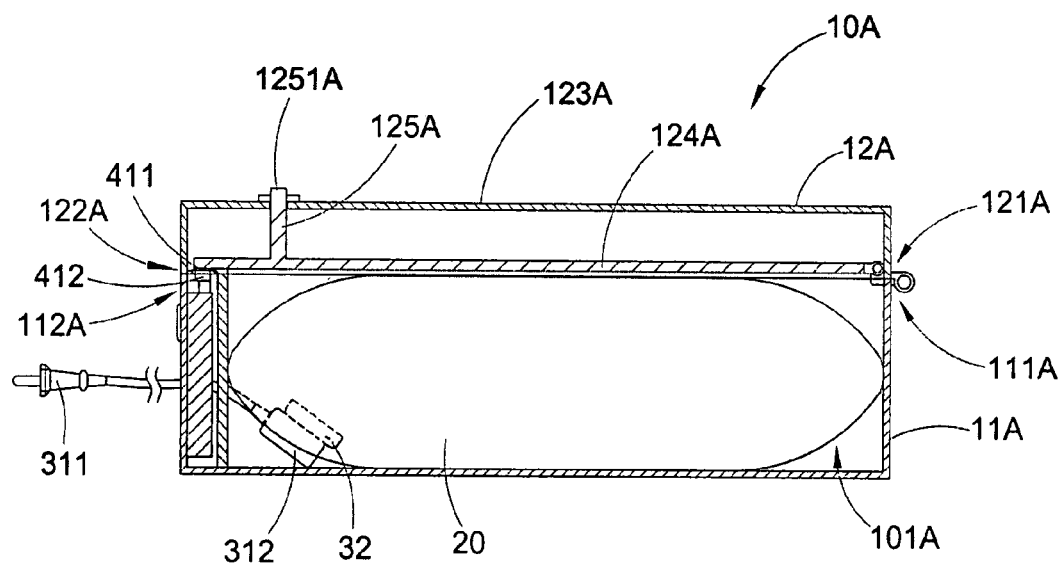
FIG. 5 illustrates a first alternative mode of the casing incorporating with the safety arrangement according to the preferred embodiment of the present invention, illustrating the warmer bag during heating operation.

FIG. 5 illustrates a first alternative mode of the casing 10A incorporating with the safety arrangement 40. The casing 10A comprises a base housing 11A and a cover housing 12A pivotally coupling with the base housing 11A to enclose the receiving compartment 101A. The base housing 11A has a first housing edge 111A and an opposed second housing edge 121A. The cover housing 12A has a pivot edge 121A pivotally coupling with the first housing edge 111A of the base housing 11A and a folding edge 122A folded to align with the second housing edge 112A of the base housing 11A. It is worth to mention that when the warmer bag 20 is disposed in the casing 10A, the two sides of the warmer bag 20 are biased against two inner sidewalls of the casing 10A respectively. Therefore, the warmer bag 20 will be expanded at its transverse direction.

The first contacting terminal 411 of the contact switch 41 is provided at the second housing edge 112A of the base housing 11A and a second contacting terminal 412 is provided at the folding edge 122A of the cover housing 12A to align with the first contacting terminal 411.

The cover housing 12A comprises an outer shelter 123A pivotally folded on the base housing 11A to enclose the receiving compartment 101A, and an inner pivot cover 124A pivotally coupling with the outer shelter 123A, wherein the second contacting terminal 412 is provided at the inner pivot cover 124A such that when the warmer bag 20 is expanded to pivotally and upwardly move the inner pivot cover 124A for moving the second contacting terminal 412 away from the first contacting terminal 411, the outer shelter 123A is remained at its position to enclose the warmer bag 20 in the receiving compartment 101A.

The cover housing 12A further comprises an operation shaft 125A having an affixing end affixed to the inner pivot cover 124A and an enlarged head 1251A which is extended through the outer shelter 123A and is arranged in such a manner that when the enlarged head 1251A is sat on the outer shelter 123A, the second contacting terminal 412 is contacted with the first contacting terminal 411, and when the enlarged head 1251A is lifted above the outer shelter 123A, the inner pivot cover 124A is pivotally lifted up to move the second contacting terminal 412 away from the first contacting terminal 411.

Figure 7:
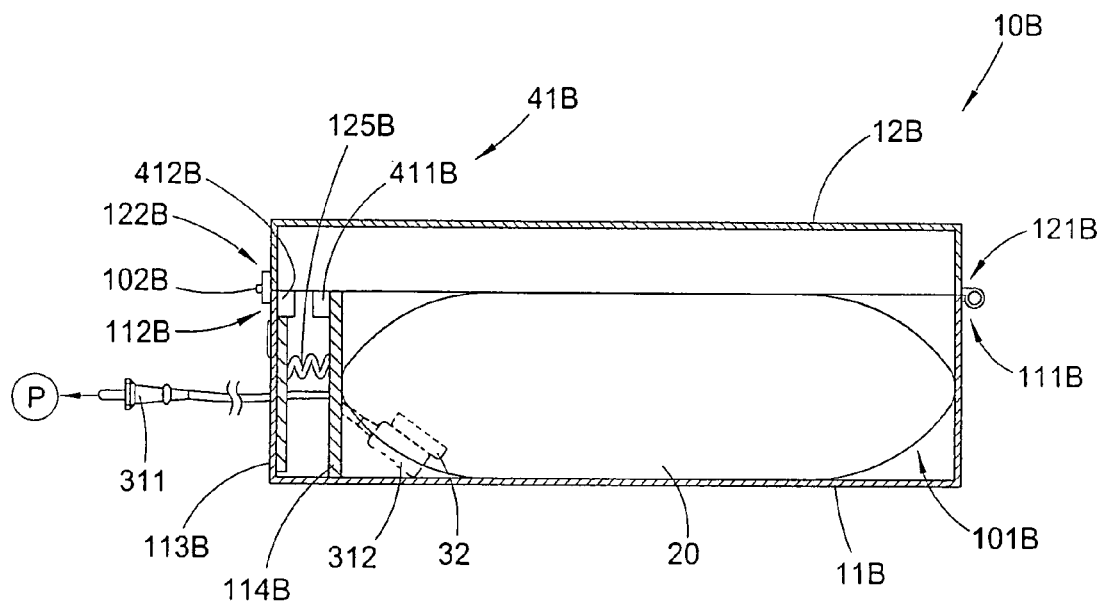
FIG. 7 illustrates a second alternative mode of the casing incorporating with the safety arrangement according to the preferred embodiment of the present invention, illustrating the warmer bag during heating operation.
Figure 8:
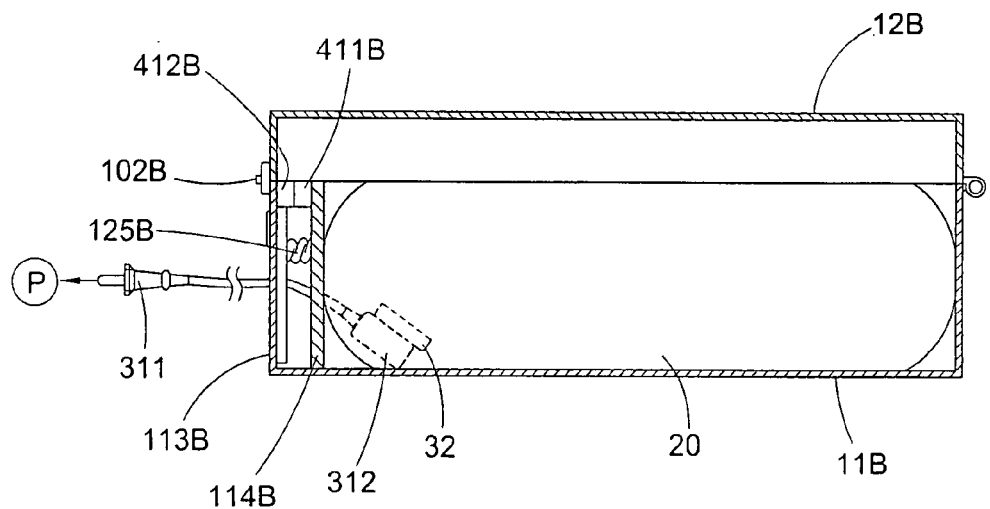
FIG. 8 illustrates the second alternative mode of the casing incorporating with the safety arrangement according to the preferred embodiment of the present invention, illustrating the warmer bag during cut off operation.

FIGS. 7 and 8 illustrate a second alternative mode of the casing 10B incorporating with the safety arrangement 40B. The casing 10B comprises a base housing 11B and a cover housing 12B pivotally coupling with the base housing 11B to enclose the receiving compartment 101B. The base housing 11B has a first housing edge 111B and an opposed second housing edge 121B. The cover housing 12B has a pivot edge 121B pivotally coupling with the first housing edge 111B of the base housing 11B and a folding edge 122B folded to align with the second housing edge 112B of the base housing 11B. A locker 102B is provided to lock up the cover housing 12B with the base housing 11B.

The base housing 11B comprises an outer affixing wall 113B and an inner movable wall 114B slidably supported within the receiving compartment 101, wherein when the heat exchanging fluid 22 is at the normal room temperature, the movable wall 114B is positioned apart from the affixing wall 113B and when the heat exchanging fluid 22 is at the usable temperature, the warmer bag 20 is expanded to move the movable wall 114B towards the affixing wall 113B. It is worth to mention that when the warmer bag 20 is disposed in the casing 10B, the top and bottom sides of the warmer bag 20 are biased against the inner top side and the inner bottom side of the casing 10B respectively. Therefore, the warmer bag 20 will be expanded at its longitudinal direction.

As shown in FIG. 7, the first contacting terminal 411B of the contact switch 41B is provided at the affixing wall 113B of the base housing 11B and the second contacting terminal 412B is provided at the movable wall 114B of the base housing 11B to align with the first contacting terminal 411B. Accordingly, the contact switch 41B keeps the electrical connection between the heating element 33 and the external power source P when the movable wall 114B is positioned apart from the affixing wall 113B to separate the second contacting terminal 412B from the first contacting terminal 411B. When the heat exchanging fluid 22 is at the usable temperature, the warmer bag 20 is expanded to move the movable wall 114B towards the affixing wall 113B to contact the second contacting terminal 412B with the first contacting terminal 411B such that the contact switch 41B cuts off the electrical connection between the heating element 33 and the external power source P. In other words, when the movable wall 114B is positioned apart from the affixing wall 113B, the second contacting terminal 412B is non-contacted with the first contacting terminal 411B to keep the electrical connection between the heating element 33 and the external power source P, and when the movable wall 114B is moved to the affixing wall 113B, the second contacting terminal 412B is contacted with the first contacting terminal 411B to cut off the electrical connection between the heating element 33 and the external power source P.

As shown in FIGS. 7 and 8, the base housing 11B further comprises a resilient element 125B supported between the affixing wall 113B and the movable wall 114B for applying an urging force against the movable wall 114B to ensure the second contacting terminal 412B being non-contacted with the first contacting terminal 411B when the heat exchanging fluid 22 is heated under the normal room temperature.

Figure 9:
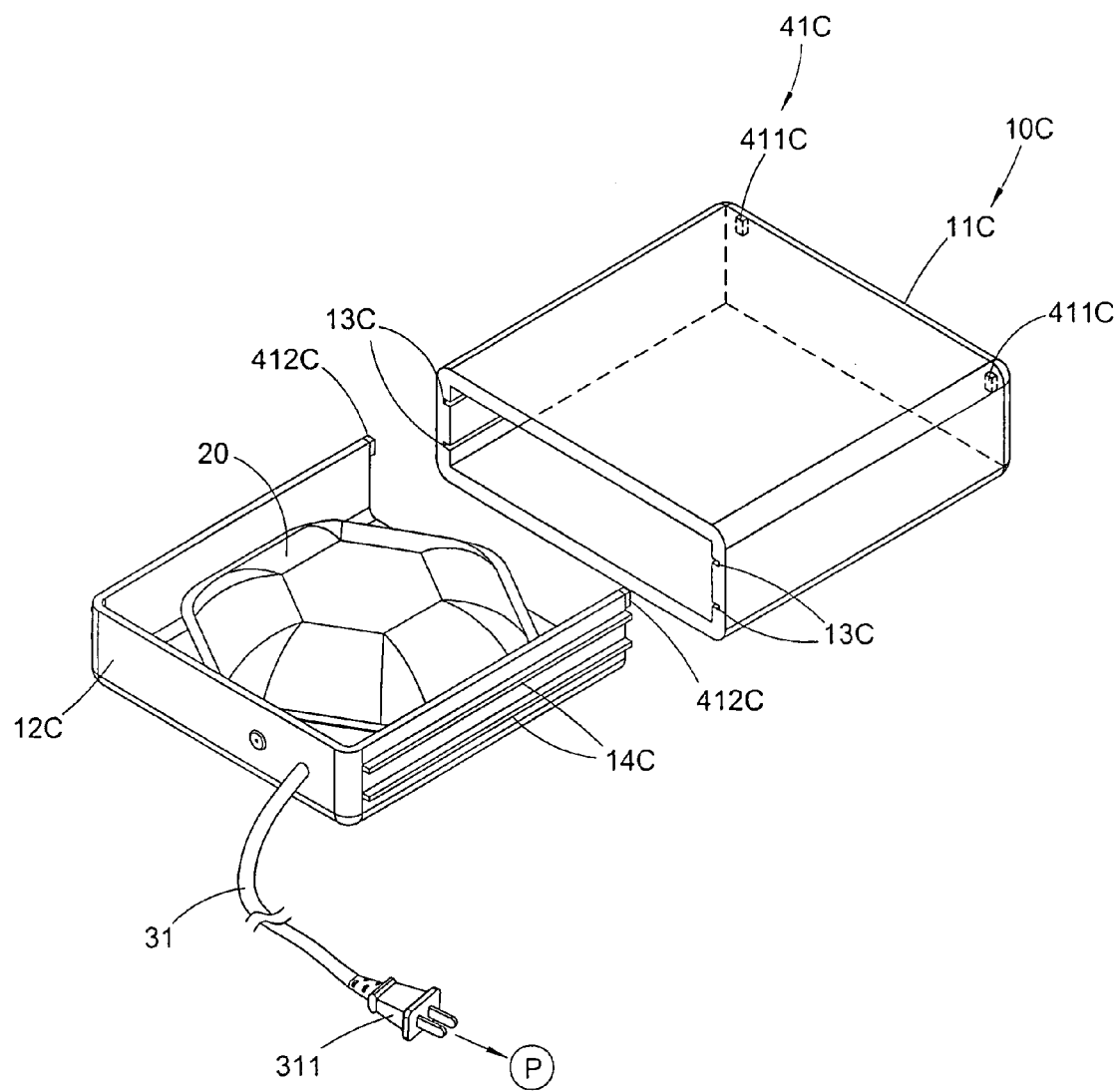
FIG. 9 illustrates a third alternative mode of the casing incorporating with the safety arrangement according to the preferred embodiment of the present invention.

FIG. 9 illustrates a third alternative mode of the casing 10C. The casing 10C comprises a hollow shaped stationary housing 11C having an opening end and an opposed wall end, and a U-shaped cross sectional sliding housing 12C slidably received in the stationary housing 11C for the warmer bag 20 disposing within the stationary housing 11C, wherein the contact switch 41C provided at the casing to cut off the electrical connection between the heating element 33 and the external power source P when the heat exchanging fluid 22 is heated at the usable temperature.

Figure 10:
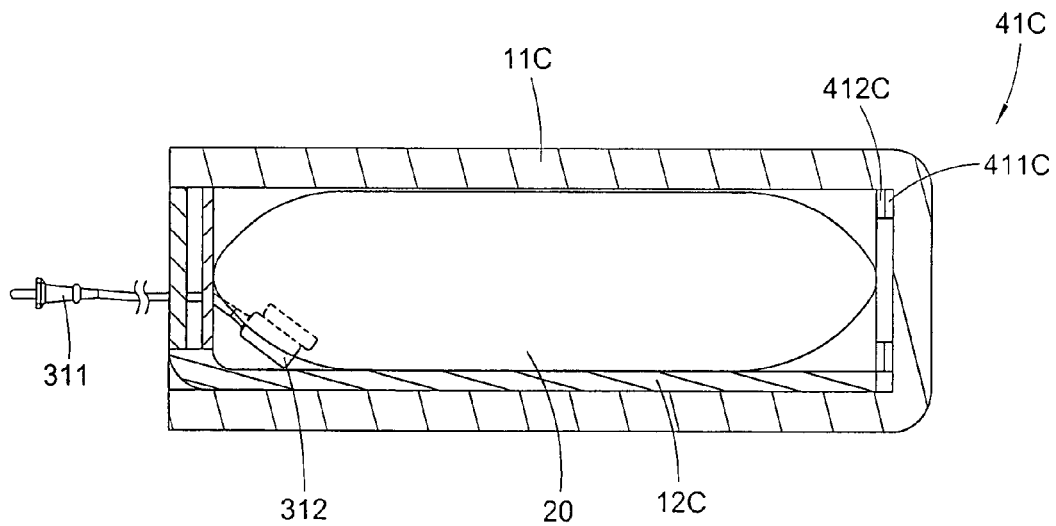
FIG. 10 illustrates the third alternative mode of the casing incorporating with the safety arrangement according to the preferred embodiment of the present invention, illustrating the warmer bag during heating operation.
Figure 11:
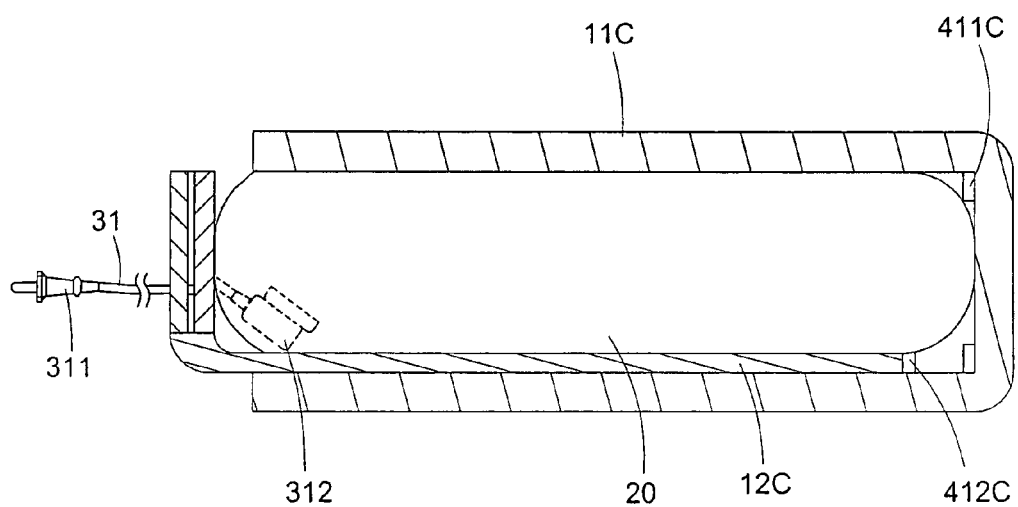
FIG. 11 illustrates the third alternative mode of the casing incorporating with the safety arrangement according to the preferred embodiment of the present invention, illustrating the warmer bag during cut off operation.

Accordingly, the contact switch 41C, which is electrically coupled with the power cable 31 between the power outlet 311 and the power adapter 312, comprises a first contacting terminal 411C provided at the wall end of the stationary housing 11C and a second contacting terminal 412C which is provided at a corresponding edge of the sliding housing 12C to align with the first contacting terminal 411C and is arranged in such a manner that when the heat exchanging fluid 22 is at the normal temperature, the sliding housing 12C is received in the stationary housing 11C to contact the second contacting terminal 412C with the first contacting terminal 411C to close the electrical connection between the heating element 33 and the external power source P, as shown in FIG. 10, and when the heat exchanging fluid 22 is at the usable temperature, the warmer bag 20 is expanded to slidably push the sliding housing 12C to move the second contacting terminal 412C away from the first contacting terminal 411C so as to cut off the electrical connection between the heating element 33 and the external power source P, as shown in FIG. 11.

It is worth to mention that when the warmer bag 20 is disposed in the casing 10C, the top and bottom sides of the warmer bag 20 are biased against the inner top side and the inner bottom side of the casing 10C respectively. Therefore, the warmer bag 20 will be expanded at its longitudinal direction.

In order to guide the contact between the first and second contacting terminals 411C, 412C, the casing 10C further contains two or more sliding tracks 13C provided at two sidewalls of the stationary housing 11C respectively and comprises two or more sliding guiders 14C provided at two sidewalls of the sliding housing 12C to slidably engage with the sliding tracks 13C respectively so as to guide the sliding housing 12C being slid within the stationary housing 11C and to ensure the second contacting terminal 412C being aligned with the first contacting terminal 411C.

Figure 12:
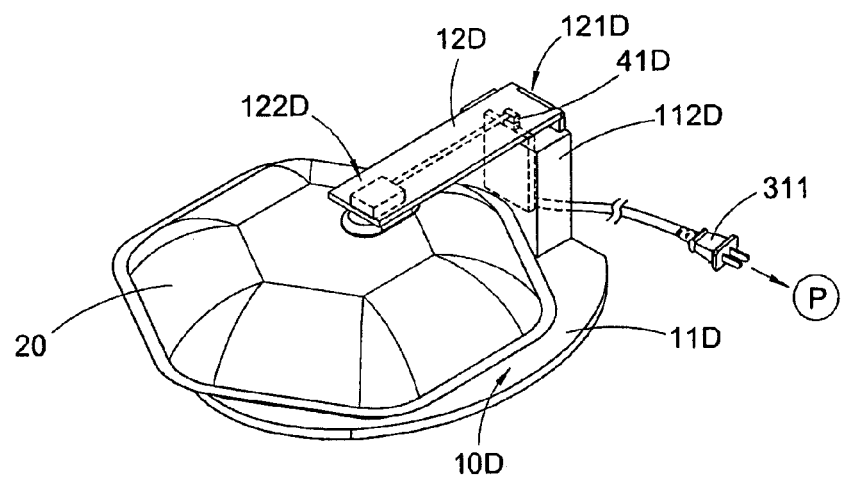
FIG. 12 illustrates a fourth alternative mode of the casing incorporating with the safety arrangement according to the preferred embodiment of the present invention.

FIG. 12 illustrates a fourth alternative mode of the casing 10D in which the warmer bag 20 is not fully concealed in the casing 10D. The casing 10D comprises a base housing 11D and a pivot arm 12D. The base housing 11D comprises a supporting platform 111D for the warmer bag 20 supporting thereon and a supporting shaft 112D upwardly extended from the supporting platform 111D. The pivot arm 12D has a pivot end 121D pivotally coupling at a top end of the supporting shaft 112D and a contacting end 122D sitting on top of the warmer bag 20.

Figure 13:
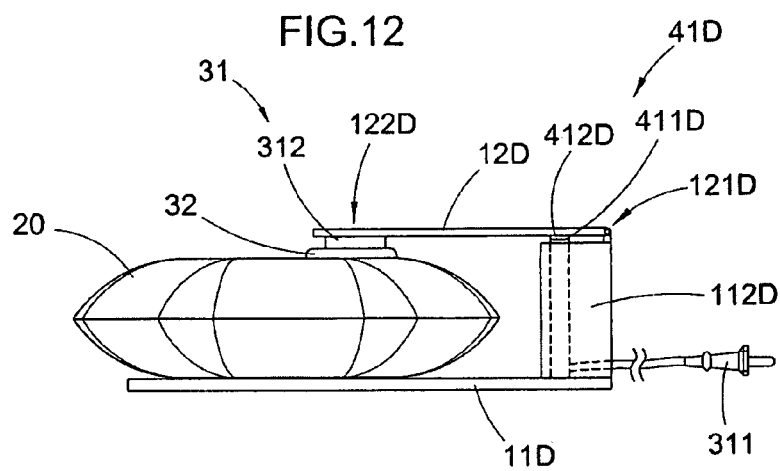
FIG. 13 illustrates the fourth alternative mode of the casing incorporating with the safety arrangement according to the preferred embodiment of the present invention, illustrating the warmer bag during heating operation.
Figure 14:
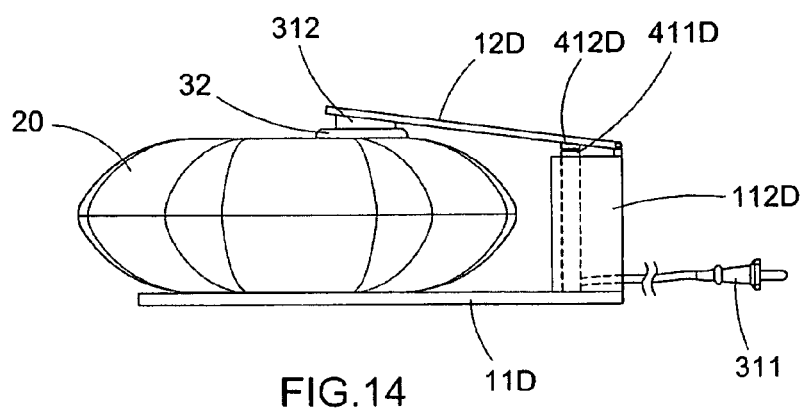
FIG. 14 illustrates the fourth alternative mode of the casing incorporating with the safety arrangement according to the preferred embodiment of the present invention, illustrating the warmer bag during cut off operation.

The contact switch 41D is provided at the casing 10D to cut off the electrical connection between the heating element 33 and the external power source P when the heat exchanging fluid 22 is heated at the usable temperature. Accordingly, the contact switch 41D is electrically coupled with the power cable 31 between the power outlet 311 and the power adapter 312. As shown in FIGS. 12 to 14, the power adapter 312 is provided at the contacting end 122D of the pivot arm 12D to electrically couple with the electric terminal 32 at the warmer bag 20.

The contact switch 41D comprises a first contacting terminal 411D provided at the top end of the supporting shaft 112D and a second contacting terminal 412D which is provided at the pivot arm 12D to align with the first contacting terminal 411D and is arranged in such a manner that when the heat exchanging fluid 22 is at the normal temperature, the second contacting terminal 412D is contacted with the first contacting terminal 411D to close the electrical connection between the heating element 33 and the external power source P, as shown in FIG. 13, and when the heat exchanging fluid 22 is at the usable temperature, the warmer bag 20 is expanded to upwardly lifted the contacting end 122D of the pivot arm 12D for moving the second contacting terminal 412D away from the first contacting terminal 411D so as to cut off the electrical connection between the heating element 33 and the external power source P, as shown in FIG. 14. It is worth to mention that the second contacting terminal 412D is provided at the pivot arm 12D at a position between the pivot end 121D and the contacting end 122D to align with the first contacting terminal 411D.

Figure 6:
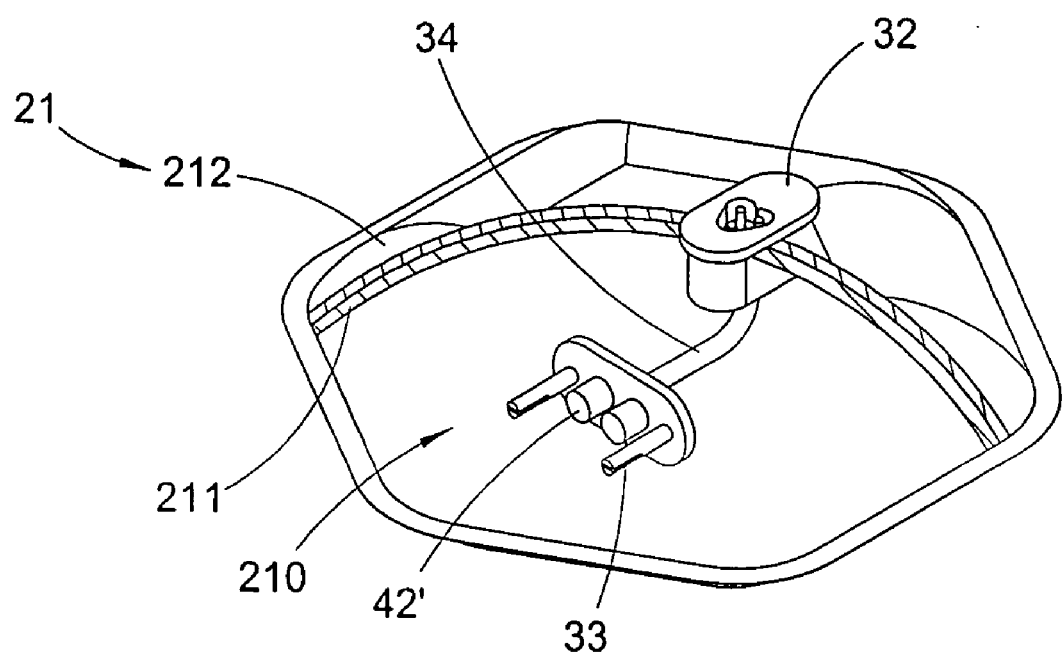
FIG. 6 illustrates an alternative mode of the safety arrangement according to the preferred embodiment of the present invention.

FIG. 6 illustrates an alternative mode of the safety arrangement 40'. The safety arrangement 40' comprises a temperature sensor 42' electrically coupling with the electric terminal 32 at a position within the fluid cavity 210 and arranged to cut off the electrical connection between the heating element 33 and the external power source P when the temperature sensor 42' detects the heat exchanging fluid 22 above the usable temperature.

Accordingly, the retention arm 34 is extended from the electric terminal 32 to the heating element 33 to retain the heating element 33 at a position that the heating element 33 is submerged at the heat exchanging fluid 22 to effectively heat up the heat exchanging fluid 22. The temperature sensor 42' is coupled with the retention arm 34 at a position adjacent to the heating element 33 to detect the temperature of the heat exchanging fluid 22.

It is worth to mention that the temperature sensor 42' can be incorporated with the above mentioned casing 10 and its alternatives to provide dual-safety feature to prevent the heat exchanging fluid 22 from being overheated.

One skilled in the art will understand that the embodiment of the present invention as shown in the drawings and described above is exemplary only and not intended to be limiting.

It will thus be seen that the objects of the present invention have been fully and effectively accomplished. The embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A portable warmer, comprising:

a casing having a receiving compartment;

a warmer bag comprising a bag body defining a fluid cavity therein, and a heat exchanging fluid sealed and contained in said fluid cavity of said bag body;

a heating arrangement comprising a power cable having a power outlet extended out of said casing for electrically connecting with an external power source and a power adapter extended into said receiving compartment, an electric terminal provided at said bag body, and a heating element which is supported in said fluid cavity and is electrically coupled with said electric terminal, wherein when said warmer bag is disposed in said receiving compartment, said power adapter of said power cable is detachably and electrically coupled with said electric terminal for electrically connecting said heating element with said external power source so as to heat up said heat exchanging fluid at a predetermined usable temperature; and a safety arrangement electrically coupling with said heating arrangement, wherein when said heat exchanging fluid is heated above said usable temperature, said safety arrangement automatically cuts off an electrical connection between said heating element and said external power source for preventing said heat exchanging fluid from being overheated;

wherein said warmer bag is made of flexible material that said warmer bag seals and contains said heat exchanging fluid in a stretchable manner, wherein when said heat exchanging fluid is at said usable temperature, said heat exchanging fluid expands its volume in comparison with said heat exchanging fluid at a normal room temperature, wherein said safety arrangement comprises a contact switch provided at said casing to cut off said electrical connection between said heating element and said external power source when said heat exchanging fluid is heated at said usable temperature;

wherein said casing comprises a base housing having a supporting platform for said warmer bag supporting thereon and a supporting shaft upwardly extended from said supporting platform, and a pivot arm having a pivot end pivotally coupling at a top end of said supporting shaft and a contacting end sitting on top of said warmer bag, wherein said contact switch provided at said casing to cut off said electrical connection between said heating element and said external power source when said heat exchanging fluid is heated at said usable temperature.

2. The portable warmer, as recited in claim 1, wherein said contact switch, which is electrically coupled with said power cable between said power outlet and said power adapter, comprises a first contacting terminal provided at said top end of said supporting shaft and a second contacting terminal which is provided at said pivot arm to align with said first contacting terminal and is arranged in such a manner that when said heat exchanging fluid is at said normal temperature, said second contacting terminal is contacted with said first contacting terminal to close said electrical connection between said heating element and said external power source, and when said heat exchanging fluid is at said usable temperature, said warmer bag is expanded to upwardly lifted said contacting end of said pivot arm for moving said second contacting terminal away from said first contacting terminal so as to cut off said electrical connection between said heating element and said external power source.

3. The portable warmer, as recited in claim 2, wherein said heat exchanging fluid is partially filled in said warmer bag that when said warmer bag is disposed in said casing, a bottom portion of said warmer bag is filled with said heat exchanging fluid while an upper portion of said warmer bag is filled with gas, wherein said heating arrangement further comprises a retention arm extended from said electric terminal to said heating element to retain said heating element at a position that said heating element is submerged at said heat exchanging fluid to effectively heat up said heat exchanging fluid.

* * * * *